United States Patent [19]

Hoffman

[11] Patent Number: 4,682,605
[45] Date of Patent: Jul. 28, 1987

[54] LIQUID CRYSTAL MATRIX FOR EXTENDED RANGE HIGH RESOLUTION TEMPERATURE MAPPING

[75] Inventor: Kent C. Hoffman, Cockeysville, Md.

[73] Assignee: Murray Electronics Associates Limited, Hunt Valley, Md.

[21] Appl. No.: 783,093

[22] Filed: Oct. 2, 1985

[51] Int. Cl.[4] .............................................. A61B 10/00
[52] U.S. Cl. ................................... 128/736; 374/137; 374/162
[58] Field of Search ................ 128/736; 374/124, 137, 374/158, 162, 208, 210

[56] References Cited

U.S. PATENT DOCUMENTS

| Re. 32,000 | 10/1985 | Sagi | 128/736 |
| 3,661,142 | 5/1972 | Flam | 128/736 X |
| 4,060,654 | 11/1977 | Quenneville | 128/736 X |
| 4,509,533 | 4/1985 | Chervitz | 128/736 |
| 4,524,778 | 6/1985 | Brown, Jr. et al. | 128/736 |

FOREIGN PATENT DOCUMENTS 2060879  5/1981  United Kingdom ............... 128/736

*Primary Examiner*—Kyle L. Howell
*Assistant Examiner*—Angela D. Sykes
*Attorney, Agent, or Firm*—Nixon & Vanderhye

[57] ABSTRACT

A recurrent matrix pattern of clusters of different narrow range temperature sensitive liquid crystal dots is disclosed. At each location on the matrix, there is a plurality of liquid crystal dots forming a cluster. Each liquid crystal dot of a cluster changes color at a different temperature. Further, each liquid crystal dot is sensitive, that is changes colors, in a very narrow temperature range. With this recurrent matrix arrangement, detailed temperature resolution can be maintained over a relatively broad temperature range, while still retaining an essentially continuous layer of temperature sensitive material so as to map-locate temperature gradients.

31 Claims, 13 Drawing Figures

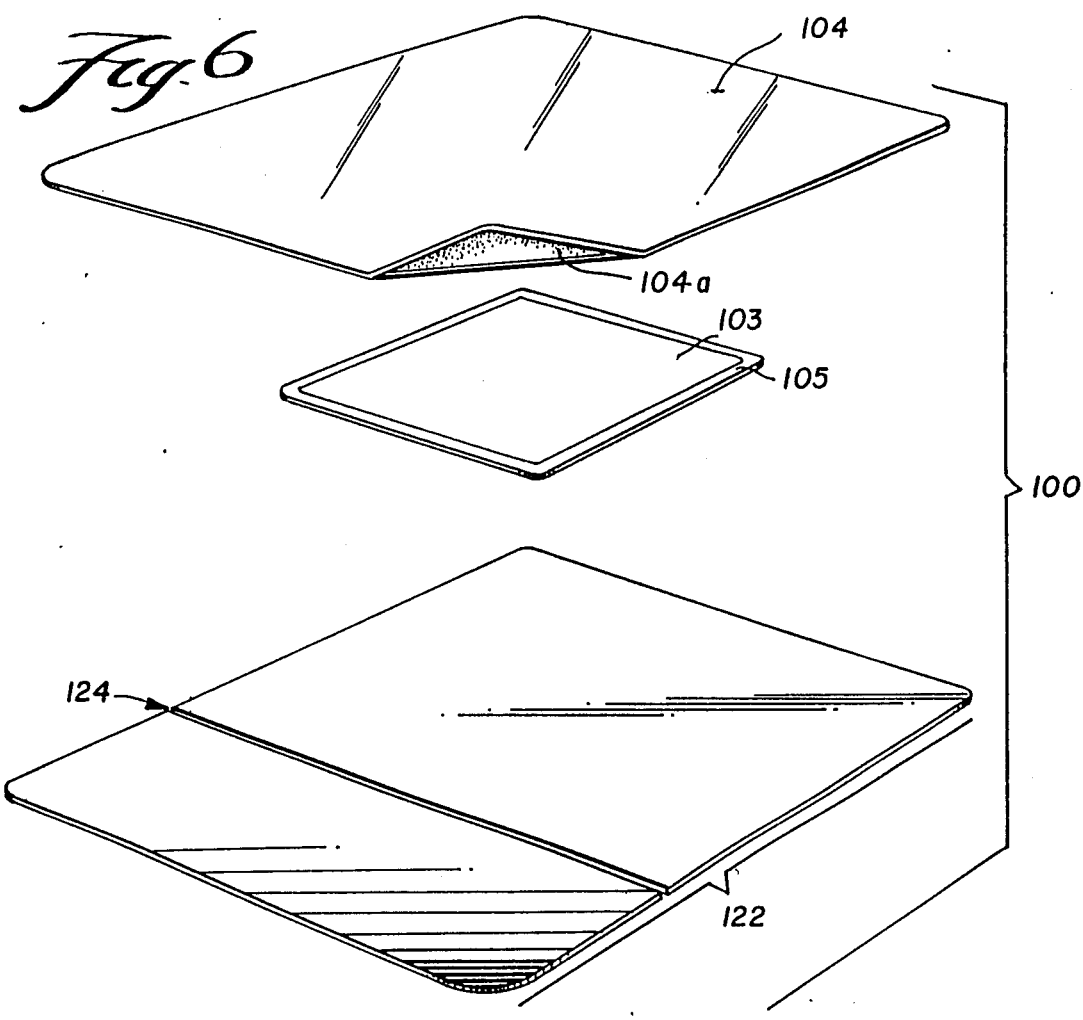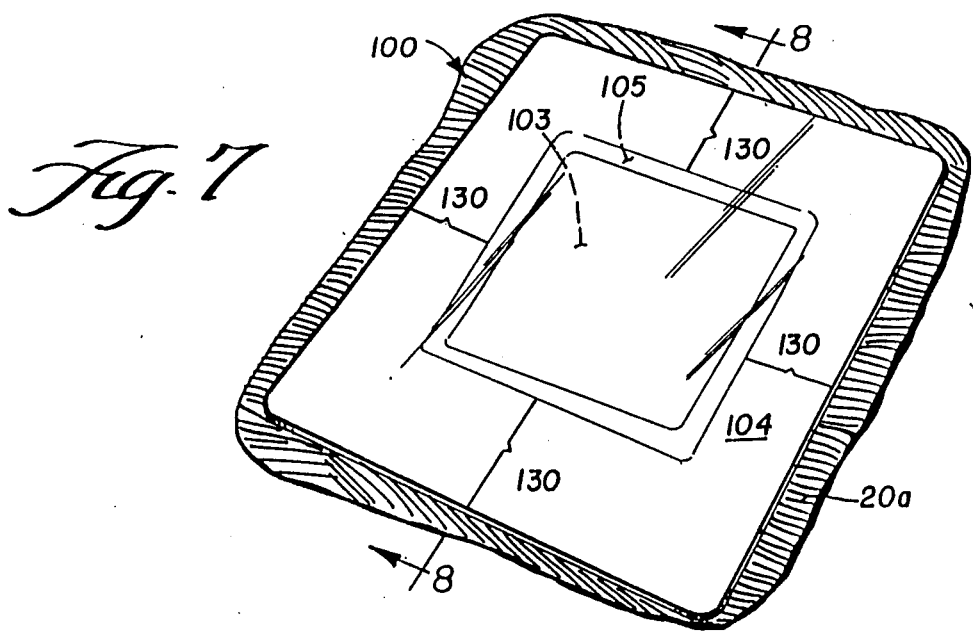

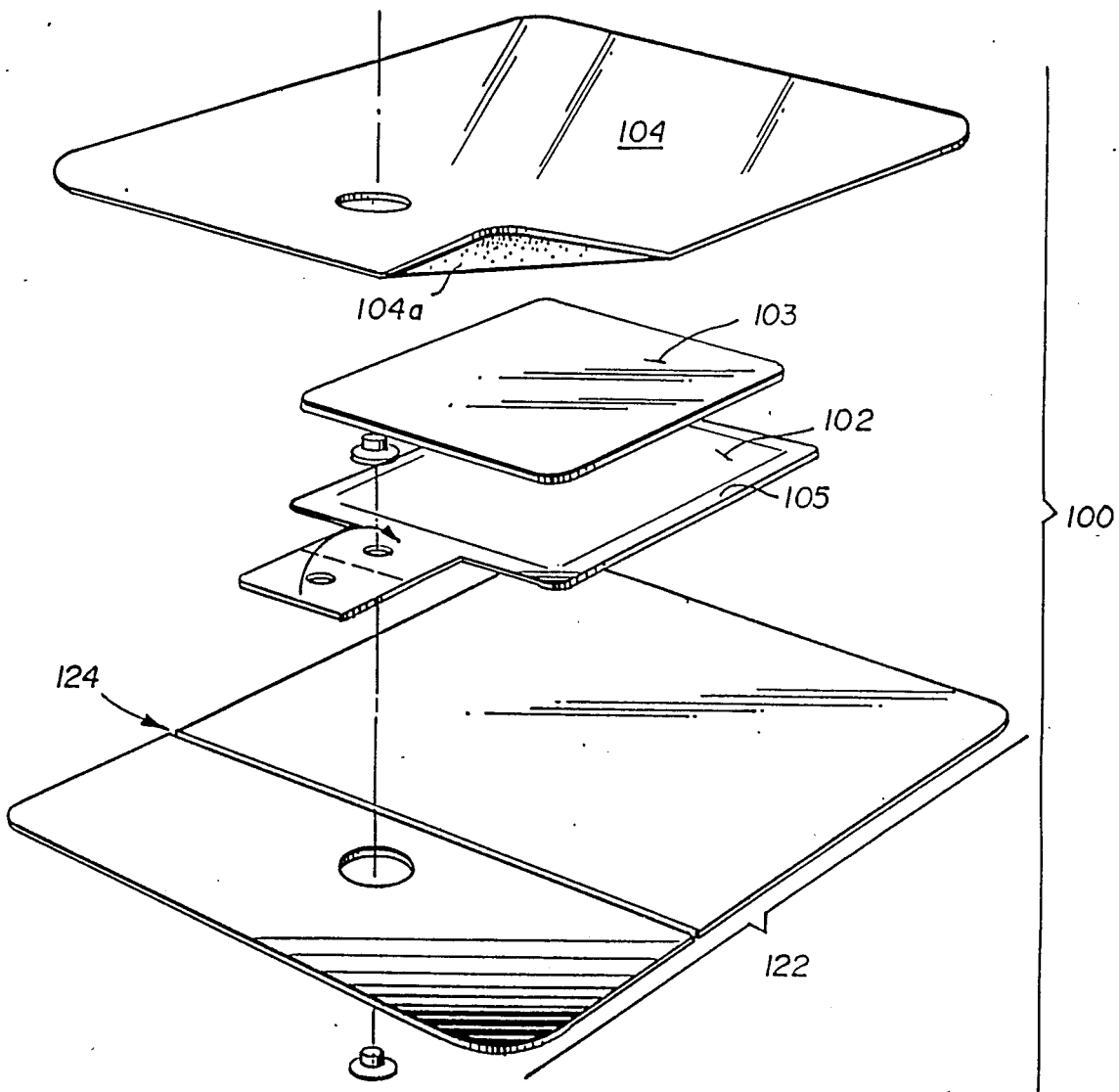

LIQUID CRYSTAL MATRIX FOR EXTENDED RANGE HIGH RESOLUTION TEMPERATURE MAPPING

This invention is generally directed to a liquid crystal matrix for extended range high resolution temperature mapping. The subject invention is related to the copending and commonly assigned applications U.S. patent application Ser. Nos. 711,044, 718,215 and 788,216, the entire disclosures of which are hereby incorporated by reference.

BACKGROUND OF THE INVENTION

Medical research has applied advanced temperature measurement techniques such as infrared thermography and liquid crystal films to diagnose and identify various forms of vascular diseases and tumors. Since temperature is an indicator of circulatory function, techniques have been developed to measure the effects of nerve blocking drugs on the circulatory system by measuring temperature. In addition to diagnostic applications, temperature measuring devices have been used in medicine to locate everything from veins to placental attachment sites.

A recent invention using liquid crystals (U.S. Pat. No. 4,378,808) can be used to detect unwanted infusion of fluids into tissue when an IV fails. U.S. Pat. No. 4,064,872 discloses a device for measuring temperature differentials on skin surfaces comprising dots of liquid crystals sealed between thin films. U.S. Pat. No. 3,951,133 discloses two or more sheets of liquid crystal thermal films assembled side by side where each sheet changes color at a different temperature. U.S. Pat. No. 4,154,106 discloses a disposable temperature indicator with an array of dots of crystals sensitive to respectively different temperature ranges.

Temperature measurement has also been used for therapeutic purposes in the field of biofeedback. A variable signal tone, light or meter provides the patient with a feedback signal that relates to the patient's skin temperature. The patient is trained to respond to this type of feedback by modifying his temperature and/or behavior.

Liquid-crystal technology has been used for numerous applications where temperature mapping is required. For example, a thin uniform coating of liquid crystals may be applied to the surface of an object to be evaluated or to a film that is coated with the liquid crystal material and then placed on the surface of an object (animate or inanimate). Liquid crystal material can be conventionally formulated to respond to either a wide temperature range or a narrow temperature range. Individually, each formulation has disadvantages. In the case of wide temperature range formulations, much valuable detail information may be lost due to lack of temperature resolution. Narrow temperature range formulations, on the other hand, offer detailed temperature resolution—but inherently can not accommodate large variations in temperature. Various systems have been devised that utilize masks to reveal numbers or symbols when liquid crystals reflect light thus allowing a number of narrow temperature range formulations to be stacked or used side by side. Although these compound systems offer more information than single formulations, they have not been very useful for mapping small details and patterns.

SUMMARY OF THE INVENTION

In brief summary, the exemplary embodiment of this invention provides a matrix pattern of clusters of liquid crystal dots of different narrow range temperature sensitive liquid crystals. At each elemental location of the matrix, there are a plurality, e.g., four liquid crystal dots forming a cluster. Each liquid crystal dot of each cluster may change color at a different temperature, and each may be color sensitive in only a very narrow range of temperature. With this recurrent matrix arrangement, detailed temperature resolution can be maintained over a broad temperature range, while still retaining an essentially continuous layer of temperature sensitive material so as to map-locate temperature gradients. The liquid crystal dots of differing temperature range sensitivity may possibly even be randomly distributed over a substrate.

These as well as other objects and advantages will be better appreciated by carefully reading the following detailed description of the presently preferred exemplary embodiments of this invention taken in conjunction with the accompanying drawings.

BRIEF DESCRIPTION OF THE DRAWINGS

FIG. 6 is an exploded perspective view of the liquid crystal matrix with means for applying the matrix to a subject;

FIGS. 7-8 are perspective and cross-sectional views of the FIG. 6 embodiment in place on the body surface of a living subject;

FIG. 11 is an exploded perspective view of the liquid crystal matrix applied to an electrode.

DETAILED DESCRIPTION OF THE INVENTION

Figure 1:
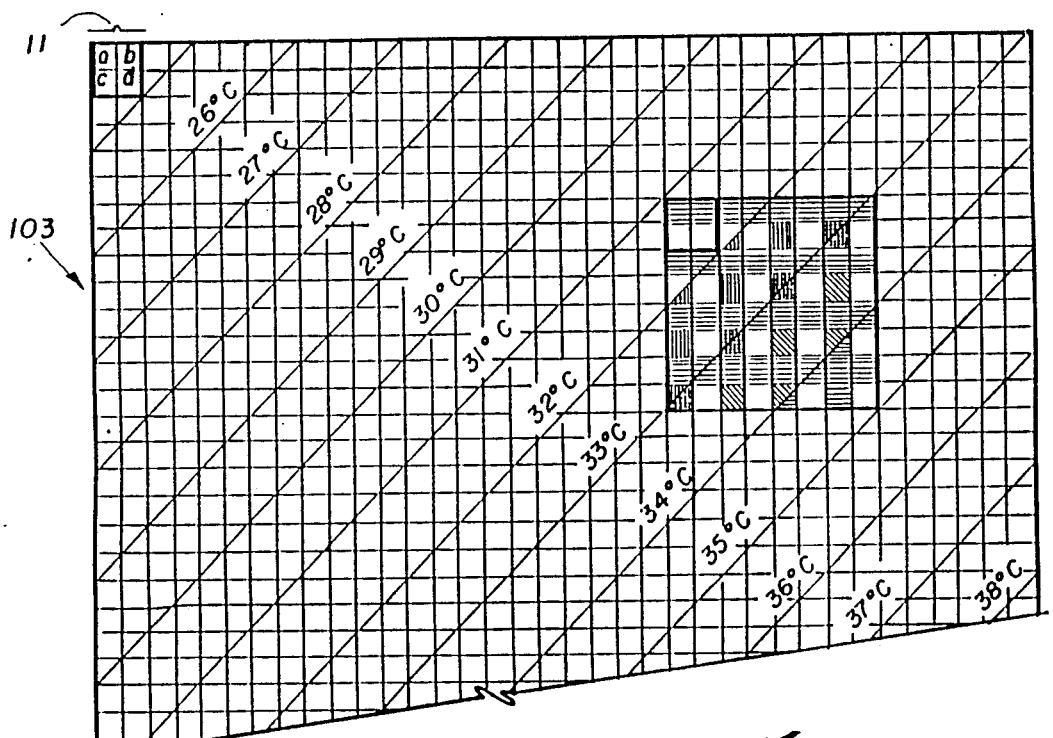
FIG. 1 is an enlarged general plan view of a section of this invention.

FIG. 1 is an enlarged view of a section of temperature gradient mapping apparatus in accordance with this invention. It includes a regularized matrix of temperature sensitive liquid crystals. In the liquid crystal matrix there is a recurrent sub-matrix pattern of dots having different narrow ranges of temperature-sensitive liquid crystals. At each elemental location of the matrix (i.e. each "pixel" position), there is a dot cluster having a plurality of liquid crystal dots. Each of the liquid crystal dots within a cluster changes colors within respectively different temperature ranges (which may overlap to some extent if desired) and each dot is sensitive to a fairly narrow range of temperature. With this recurrent matrix arrangement, detailed temperature resolution can be maintained over a broad temperature range, while still retaining an essentially continuous layer of temperature sensitive material so as to map-locate temperature gradients.

Figure 3B:
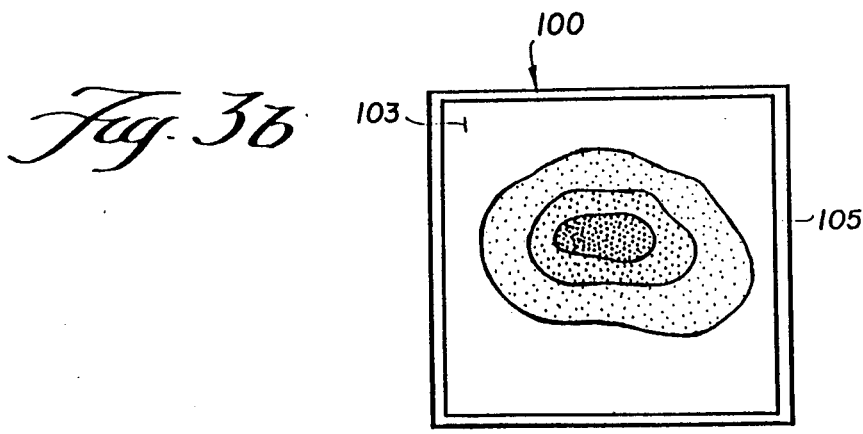
FIG. 3b is a general plan view of the invention as it appears in response to a heat source.
Figure 3A:
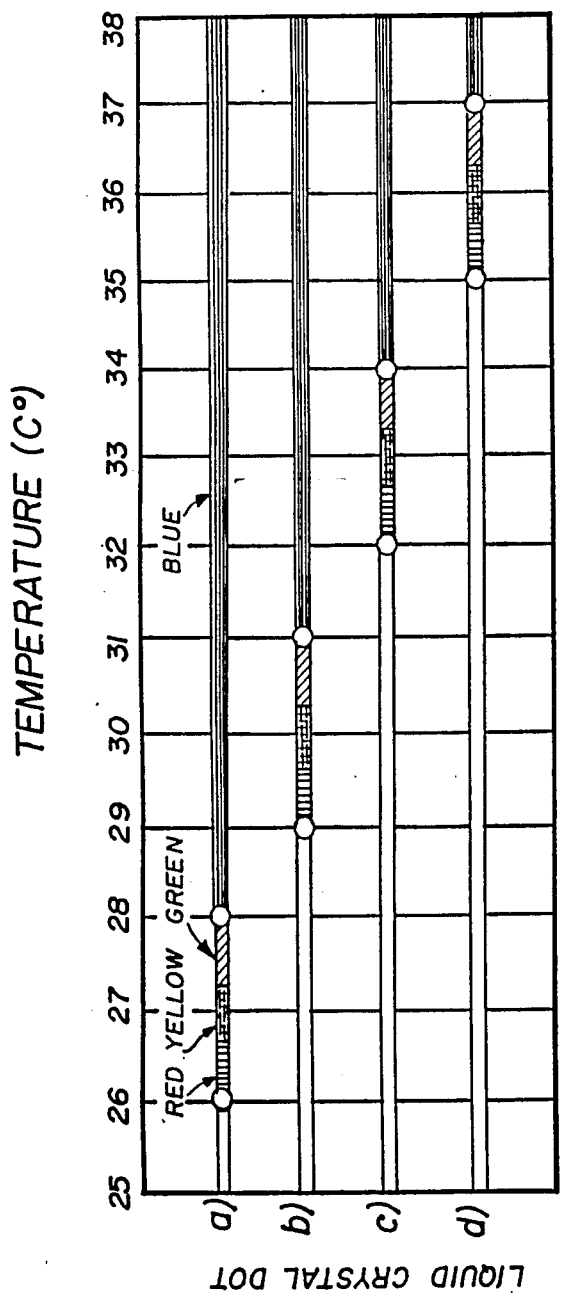
FIG. 3a is a diagram showing how four liquid crystal dots of a cluster change color with temperature.
Figure 4:
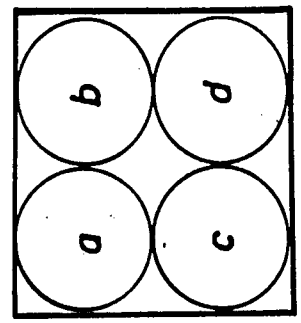
FIG. 4 is a blowup of one cluster showing four liquid crystal dots.

As an example, assume that each pixel location, e.g., 11, of the liquid crystal matrix 103 includes a cluster of four liquid crystal dots, a, b, c, and d as shown in FIGS. 1 and 4. Assume also that all four liquid crystal dots are clear colored at temperatures below that at which they turn red. Thus, they will appear the color of the background. In this example, assume a black background. For liquid crystal dot a, red starts at 26° C. and blue at 28° C. for liquid crystal dot b, red starts at 29° C. and blue at 31° C.; for dot c, red starts at 32° C. and blue at 34° C.; and for dot d, red starts at 35° C. and blue at 37° C. as shown in FIG. 3a. All four liquid crystal dots are blue within a range of temperature above that at which they first turn blue. Also, each liquid crystal goes through a color transforation as it is heated, before it becomes blue. Assume that the four liquid crystal dots change color from clear to red to yellow to green to blue as shown in FIG. 3a.

If this cluster of dots recurs over a matrix layer which is placed over a heat source surface having bands of constant temperature of from 38° to 25° C., then at the 38° C. location of the matrix, all four dots would be blue since each dot of the cluster is blue at 38° C. Moving down the temperature gradient, at a locus corresponding to a temperature just below 37° C., each cluster would have three blue dots and one green dot. At 36° C., each cluster would have three blue dots and one yellow dot. At just above 35° C., each cluster would have three blue dots and one red dot. FIG. 1 includes a section between 31° C. and 35° C. illustrating, on an enlarged scale, the color transformation of the four liquid crystal dots with temperature.

Moving down the temperature gradient to just below 31° C., there would be one blue dot, one green dot and two black dots. At 30° C., there would one blue dot, one yellow dot and two black dots. At just above 29° C., there would be one blue dot, one red dot and two black dots. Thus, although liquid crystal dot d goes through these same color changes from 37° C.-35° C. as liquid crystal dot b at 31° C.-29° C., the other crystal dots of the cluster are different in the two cases as shown in FIG. 3a: in the 35° C.-37° C. temperature range, the other crystal dots (i.e., a, b, and c) are blue, whereas in the 29° C.-31° C. range one crystal dot (a) is blue while the other two (c and d) are black. Therefore, because each liquid crystal dot is very small, the colors of the clusters in each temperature region will blend and different regions will be distinguishable by color as shown in FIG. 3b.

It is to be understood that the background can be colors other than black. Also, the range of temperatures at which each crystal dot changes from red to yellow to green to blue can be conventionally increased or decreased depending upon the application. Further, liquid crystals having different color transformation properties may be used. The dots can overlap, abut or be spaced apart. The overall size of each pixel location (i.e. the size of the submatrix which is recurrently arrayed in the larger overall matrix) may be varied as desired but is preferably sufficiently small as to make the individual dot sizes virtually imperceptible to the unaided human eye.

Figure 5:
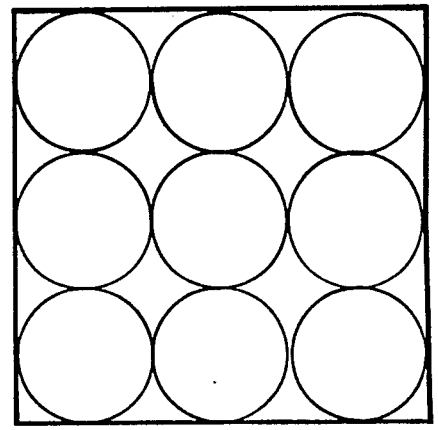
FIG. 5 is a blowup of one cluster showing nine liquid crystal dots.

Other embodiments using greater or fewer numbers of dots (each of which changes color at a different temperature) at each pixel location are possible as shown in FIG. 5. Temperature mapping of local temperature events is possible over a wide or range of temperatures if more dots are included in each cluster—as should now be apparent.

Figure 2A:
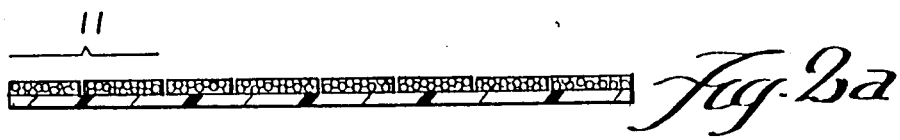
FIGS. 2a and 2b are two possible cross-sectional views of FIG. 1.

In a preferred embodiment of this invention, microencapsulated liquid crystals are screen printed onto a suitable substrate. The printing can be done in such a way that each cluster is in the form of a regularized matrix as shown in FIGS. 4 and 5, or it can be done by spraying or otherwise randomly printing approximately equal numbers of each type of dot in all areas. The substrate may be a metal foil or, advantageously, a clear plastic film (see FIG. 2a). In this embodiment the background color is applied to the substrate. Advantageously, the film may be 1-2 millimeters in thickness.

Figure 2B:
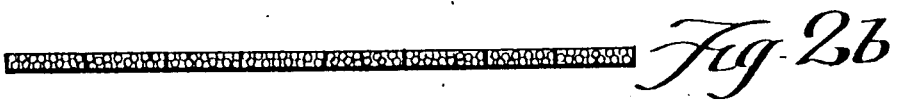

In another embodiment of the invention, the microencapsulated liquid crystals are formed into a self-sustaining layer (i.e. without a substrate) as shown in FIG. 2b. In this embodiment the background color may be applied to the underside of the liquid crystal layer 103.

The liquid crystal matrix can be affixed to the surface of a living subject or other objects using a clear adhesive tape. The tape should be clear to permit viewing of the liquid crystal matrix.

In another embodiment of the present invention, shown in FIG. 6, the liquid crystal matrix is affixed to a central portion of a flexible top film layer 104 having an adhesive coating 104a on its lower surface. The top film layer 104 with its adhesive backing 104a is larger than the underlying layer so that a band of adhesive is exposed around the outside of the lower layer. This adhesive band holds the liquid crystal layer 103 in place on the skin by adhering to the skin. The top film layer 104 with its adhesive backing 104a is clear to permit viewing of the liquid crystal layer 103 (and a printed fixed color temperature reference border). The top film layer acts as a buffer against ambient drafts which could alter the image formed by the liquid crystal layer. The top film layer also provides protection to the liquid crystal layer 103. The border 105 surrounding the liquid crystal film layer 103 may be printed with a fixed color scale and related temperature values that correspond to the liquid crystal colors.

The presently preferred adhesive-backed film 104 may be cut from commercially available material (e.g., part no. 7350 from 3M Corporation which comprises a thin (e.g., 0.002 inch) insulating sheet of polypropylene with a thin (e.g., 0.0008 inch) coating of acrylic adhesive 104a on one side).

The assembly of FIG. 6 also includes a releasable liner layer 122 which is normally in place covering the otherwise exposed portions of the adhesive surface 104a until the intended time of usage. Typically, the release liner 122 will include a break 124 so the entire assembly may be slightly bent at the break to gain finger access to a free edge of the releasable liner 122 and thus facilitate its strippage from the adhesive layer 104a and ready the assembly for adhesive fixation to the desired body surface.

Figure 8:
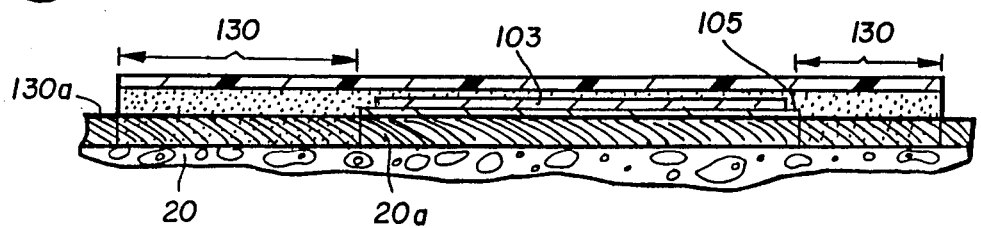

FIG. 7 depicts a liquid crystal layer with releasable liner 122 removed and the remainder of the assembly adhesively secured in place to a desired external body surface 20a of a living subject. Typically, the application site 20a should be clean and dry. Once the protective releasable liner 122 has been removed so as to expose a boundary of adhesive 104a, the assembly may be positioned as desired over the treatment site and pressed firmly thereto so as to insure a good adhesive bond. As shown in the cross-sectional view of FIG. 8, the boundary areas 130 will include an adhesively sealed and occluded area 103a which incorporates any contiguous body hair so as to provide a substantially impervious seal between the external surface of living body 20 and the periphery of the liquid crystal layer 103.

The border area 130 of adhesive should be sufficiently wide to insure good adhesive affixation. Preferably such adhesive is provided in a substantially continuous border 130 all about the liquid crystal layer 103. However, as should be appreciated, for some applications it may not be necessary to have such a continuous enclosure of the liquid crystal layer skin interface.

Figure 9:
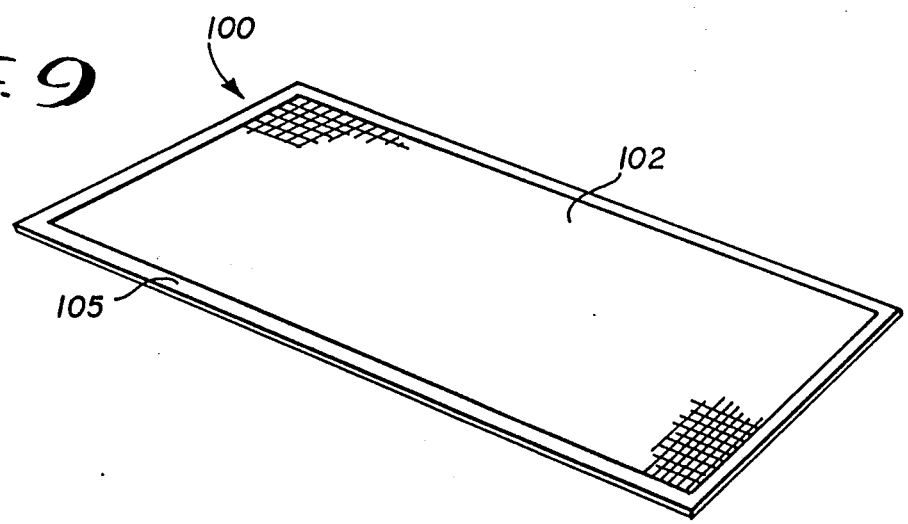
FIGS. 9-10 are perspective views of other embodiments of the invention.
Figure 10:
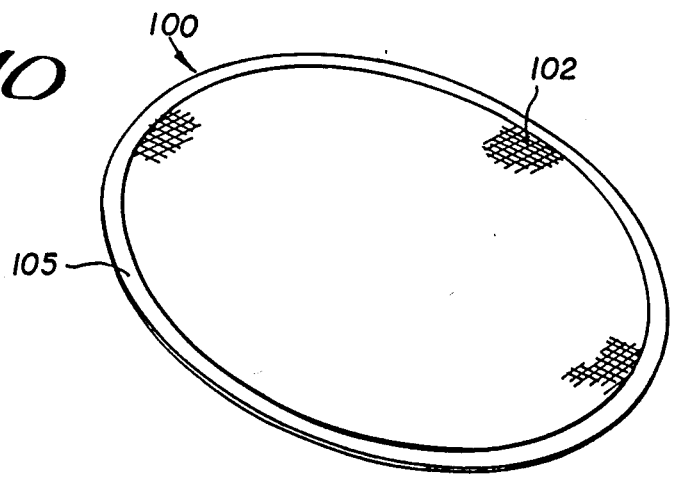

As should be appreciated, other liquid crystal layer shapes may utilize the principles of this invention, for example any elongated rectangular layer depicted in FIG. 9 or rounded layer as shown in FIG. 10. It will also be appreciated that the adhesive backing might in some cases be applied directly to the periphery or other desired portions of the liquid crystal layer itself.

In the present exemplary embodiment, the liquid crystal layer 103 is approximately 3×3 inches, while the top film layer 104 may be approximately 5×5½, inches in overall dimension.

The liquid crystal matrix of this invention may be applied to an electrode for medical or veterinary use as shown in FIG. 11. The liquid crystal layer may be used to help indicate whether the electric field applied by the electrode is having the desired effect. The liquid crystal layer may also indicate whether the electrode is properly secured to the body surface of the patient. See my copending, commonly assigned application U.S. patent application Ser. No. 788,216 for a more thorough discussion of the electrode liquid crystal matrix combination.

It should be understood that the present invention has a wide variety of applications in addition to the medical/veterinary field. The invention is useful for observing temperature gradients on any type of surface.

Although this invention has been above-described only with respect to a few presently preferred exemplary embodiments, those skilled in the art will recognize that many variations nd modifications may be made in these embodiments while yet retaining many of the novel features and advantages of this invention. The following claims are intended to cover all such variations and modifications.

What is claim is:

1. An apparatus for measuring and visually displaying temperature gradients over an extended temperature range as color-coded contours of constant temperature, said apparatus comprising;
    a first plurality of arrayed discrete deposits of liquid crystals sensitive in a first temperature range;
    a second plurality of arrayed discrete deposits of liquid crystals sensitive in a different second temperature range;
    said first and second pluralities of discrete deposits of liquid crystals being separate from one another but disposed in co-located respective sub-arrays on a common substrate to form a composite overall array of said discrete deposits in a common liquid crystal layer which responds with said color-coded contours over an extended temperature range corresponding to a combination of said first and second temperature ranges;
        said discrete deposits being of sufficiently small size and being of sufficiently large number to directly present color-coded contours of constant temperature wherein a predetermined color produced by a blended color mixture of said first and second arrayed deposits represents a corresponding predetermined temperature.

2. The apparatus of claim 1 wherein said pluralities of liquid crystals are distributed randomly.

3. The apparatus of claim 1 wherein said first and second temperature ranges are substantially adjacent temperature ranges.

4. The apparatus of claim 1 wherein said liquid crystals are micro-encapsulated.

5. The apparatus of claim 1 wherein crystals from said first and second plurality of liquid crystals are arranged to form a regularized cluster pattern; and wherein said cluster is repeated in a regularized larger matrix pattern.

6. The apparatus of claim 5 wherein said cluster comprises a first dot of liquid crystals from said first plurality of liquid crystals and a second dot of liquid crystals from said second plurality of liquid crystals; and wherein said first and second dots are arranged in a matrix pattern.

7. The apparatus of claim 6 wherein each said cluster comprises four dots arranged in a matrix pattern including a third dot of liquid crystals sensitive in a different third temperature range and a fourth dot of liquid crystals sensitive in a different fourth temperature range.

8. The apparatus of claim 6 wherein each said cluster comprises nine dots arranged in a matrix pattern including fifth through ninth dots of liquid crystals sensitive in respectively different fifth through ninth temperature ranges.

9. The apparatus of claim 1 wherein an adhesive boundary extends at least part way about the edges of said liquid crystal layer.

10. The apparatus of claim 9 wherein said adhesive boundary comprises an adhesive-backed flexible insulating sheet having said liquid crystal layer affixed therewith on one adhesive-coated side; and
    further including a release liner releasably attached to and covering the otherwise remaining exposed adhesive-backing of said sheet prior to its intended usage.

11. The apparatus of claim 1 wherein said liquid crystal layer has a border with a color-temperature reference scale imprinted thereon.

12. An apparatus for measuring and visibly displaying temperature gradients over an extended temperature range as color-coded contours of constant temperature, said apparatus comprising:
    a thin film;
    a first plurality of dots of liquid crystals sensitive in a first temperature range;
    a second plurality of dots of liquid crystals sensitive in a second temperature range;
    said first and second pluralities of dots of liquid crystals being separate from one another on one side of said thin film but disposed in co-located respective sub-arrays on a common substrate to form a composite overall array of said dots in a common liquid crystal layer which responds with said color-coded contours over an extended temperature range corresponding to a combination of said first and second temperature ranges;
    said dots being of sufficiently small size and being of sufficiently large number to directly present color-coded contours of constant temperature wherein a predetermined color produced by a blended color mixture of said first and second dots represents a corresponding predetermined temperature.

13. The apparatus of claim 12 wherein said pluralities of liquid crystals are distributed randomly.

14. The apparatus of claim 12 wherein said first and second temperature ranges are consecutive temperature ranges.

15. The apparatus of claim 12 wherein said liquid crystals are micro-encapsulated.

16. The apparatus of claim 12 wherein crystals from said first and second plurality of liquid crystals form a cluster; and wherein said cluster is repeated in a matrix pattern.

17. The apparatus of claim 16 wherein said cluster comprises a first dot of liquid crystals from said first plurality of liquid crystals and a second dot of liquid crystals from said second plurality of liquid crystals; and wherein said first and second dots are arranged in a matrix pattern.

18. The apparatus of claim 17 wherein each said cluster comprises four dots arranged in a matrix pattern including a third dot of liquid crystals sensitive in a different third temperature range and a fourth dot of liquid crystals sensitive in a different fourth temperature range.

19. The apparatus of claim 17 wherein each said cluster comprises nine dots arranged in a matrix pattern including fifth through ninth dots of liquid crystals sensitive in respectively different fifth through ninth temperature ranges.

20. The apparatus of claim 12 wherein an adhesive boundary extends at least part way about the edges of said thin film.

21. The apparatus of claim 20 wherein said adhesive boundary comprises an adhesive-backed flexible insulating sheet having said thin film with said first and second plurality of liquid crystals affixed therewith on one adhesive-coated side; and
   further including a release liner releasably attached to and covering the otherwise remaining exposed adhesive-backing of said sheet prior to its intended usage.

22. The apparatus of claim 12 wherein said thin film has a border with a fixed color-temperature reference scale imprinted thereon.

23. The apparatus of claim 12 wherein said thin film comprises plastic.

24. The apparatus of claim 12 wherein said thin film comprises metal.

25. A method of manfacturing a temperature gradient sensor comprising the step of forming, into a common layer, a plurality of regularly repeated and arrayed groups of dots of microencapsulated liquid crystals, each dot of a given group being sensitive in a different temperature range; said dots of liquid crystals within each group being separate from other dots in that group;
   said dots being of sufficiently small size and being of sufficiently large number to directly present color-coded contaours of constant temperature wherein a predetermined color produced by a blended color mixture of said first and second dots represents a corresponding predetermined temperature.

26. A method as in claim 25 including the step of forming a thin clear plastic layer over said layer of liquid crystals.

27. A method of manufacturing a temperature gradient sensor comprising the step of forming, on a thin film, a plurality of regularly repeated and arrayed groups of dots of liquid crystals, each dot of a given group being sensitive in a different temperature range; said dots of liquid crystals within each group being separate from other dots in that group;
   said dots being of sufficiently small size and being of sufficiently large number to directly present color-coded contours of constant temperature wherein a predetermined color produced by a blended color mixture of said first and second dots represents a corresponding predetermined temperature.

28. A method as in claim 27 including the step of forming a thin clear plastic layer over said thin film having liquid crystals thereon.

29. A method of manufacturing a temperature gradient sensor comprising the step of forming, on a thin film, a plurality of regularly repeated and arrayed groups of dots of liquid crystals, each dot of a given group being sensitive in a different temperature range; said dots of liquid crystals being arranged in recurrently disposed clusters of liquid crystals, wherein each cluster has liquid crystals from each of said groups;
   said dots being of sufficiently small size and being of sufficiently large number to directly present color-coded contours of constant temperature wherein a predetermined color produced by a blended color mixture of said first and second dots represents a corresponding predetermined temperature.

30. A method as in claim 29 including the step of forming a thin clear plastic layer over said thin film having liquid crystals thereon.

31. A temperature gradient mapping apparatus for high resolution visual display of temperature gradients over an extended temperature range, said apparatus comprising:
   a substrate;
   a composite matrix of temperature sensitive liquid crystal deposits distributed over said substrate;
   said composite matrix of deposits also being arranged in a regularly recurring sub-matrix pattern;
   each sub-matrix pattern having N discrete deposits therewithin of crystals with different relatively narrow ranges of temperature sensitivity ($T1a$–$T1b$ ... $TNa$–$TNb$ ...) where $TNa > TNb$ and $T1a > T2a > $ ... $TNa$ whereby the temperature resolution capability of the overall apparatus is determined by such relatively narrow individual ranges of temperature sensitivity while the extended range of temperatures over which such high resolution is attained is determined by the overall composite range $T1a$–$TNb$;
   said discrete deposits within each said sub-matrix being sized sufficiently small as to produce apparent color stimulus from the sub-matrix representing a blended color composite of the plural deposits therewithin; and
   said sub-matrix recurring with sufficient frequency and density to make the overall composite visual display produce color-coded contours of constant temperature over said extended range of temperatures;
   said discrete deposits being of sufficiently small size and being of sufficiently large number to directly present color-coded contours of constant temperature wherein a predetermined color produced by a blended color mixture of said first and second arrayed deposits represents a corresponding predetermined temperature.

* * * * *